(12) United States Patent
Duncan

(10) Patent No.: US 12,178,741 B2
(45) Date of Patent: Dec. 31, 2024

(54) COMPRESSION BODYSUIT RETRACTOR FOR BOWEL MOVEMENT

(71) Applicant: Amy Duncan, Porter, TX (US)

(72) Inventor: Amy Duncan, Porter, TX (US)

( * ) Notice: Subject to any disclaimer, the term of this patent is extended or adjusted under 35 U.S.C. 154(b) by 173 days.

(21) Appl. No.: 17/558,071

(22) Filed: Dec. 21, 2021

(65) Prior Publication Data

US 2023/0293337 A1    Sep. 21, 2023

(51) Int. Cl.
*A61F 5/451* (2006.01)
*A61F 5/44* (2006.01)

(52) U.S. Cl.
CPC ............ *A61F 5/451* (2013.01); *A61F 5/4405* (2013.01)

(58) Field of Classification Search
CPC . A61F 5/451; A61F 5/4405; A61F 2005/4415
See application file for complete search history.

(56) References Cited

U.S. PATENT DOCUMENTS

D960,358 S  *  8/2022  Wang ........................ D24/122

OTHER PUBLICATIONS

Screen captures from WayBack Machine of Alan Bilzerian online retailer, 1 page, webpage saved on Jun. 23, 2021. Retrieved from Internet: <http://web.archive.org/web/20210623121853/https://www.alanbilzerian.com/ultra-reduction-ridge-bracelet/> (Year: 2021).*
Evan Sugerman, Parts of 4—Ultra Reduction Ridge Bracelet 15mm, Nov. 16, 2018, Instagram, Retrieved from Internet: <https://www.instagram.com/p/BqPZfXLFBF3/?igsh=aGt6bDZhaGs5d2Zs> (Year: 2018).*

* cited by examiner

*Primary Examiner* — Catharine L Anderson
*Assistant Examiner* — Erin A Kim
(74) *Attorney, Agent, or Firm* — DUREN IP; Todd E. Zenger

(57) ABSTRACT

The present invention is directed to an apparatus used during a bowel movement while the user is wearing a compression bodysuit such that feces do not soil the compression bodysuit. The apparatus may include a seat that rests against the skin, a chute/shield to allow for passage of feces into the toilet, and a support that keeps the apparatus in place to facilitate pulling a compression bodysuit back and away from the anal area. The apparatus is designed to allow feces to fall into the toilet without getting on the compression bodysuit and without contacting the apparatus. In the occurrence of abnormal or watery stools the apparatus functions as a splatter shield to block feces from soiling the compression bodysuit.

18 Claims, 6 Drawing Sheets

COMPRESSION BODYSUIT RETRACTOR FOR BOWEL MOVEMENT

This application claims the benefit under section 119(e) of U.S. Provisional Application No. 65/151,043 filed Feb. 18, 2021.

1. FIELD OF THE INVENTION

The present invention relates to an apparatus which allows men and women to have a bowel-movement without removing their compression bodysuit and without getting feces on their compression bodysuit.

Compression bodysuits are often required to be worn continuously for periods of time after some surgeries such as liposuction, cosmetic surgeries, or postpartum and are used as aesthetic body shaping garments. The apparatus of the present invention is an accessory to the compression bodysuit.

The compression bodysuit has an opening to allow for urination and bowel movements. Because of the nature of the compression bodysuit having to provide support in all areas of the body, the opening is often not sufficient enough, resulting in urine and feces getting on the compression bodysuit while using the toilet. The disclosed apparatus of the present invention pulls back the compression bodysuit to facilitate bowel movements so that feces does not get on the bodysuit garment.

The apparatus of the present invention retracts or draws back the anal area of the compression bodysuit to allow the wearer to have a bowel movement without getting feces in or on the compression bodysuit and without needing to remove the compression bodysuit. The intended use of the present invention is to pull the garment back in the anal area and allow passage of feces into the toilet without getting on the apparatus or compression bodysuit.

2. BACKGROUND AND RELATED ART

Current compression garments are used to help permanently mold the human body to acquire a specific body shape, reduce swelling and inflammation after surgery, postpartum, after liposuction, and are worn under clothing to acquire a temporary body shape such as a female hourglass figure. Some of these garments include girdles, fajas, compression garments for various parts of the body, and a full body compression garment referred to hereinafter as a compression bodysuit. A compression bodysuit is made from a very strong, stretchy, high tension strength fabric with an opening in the crotch or anal area. Compression bodysuits have a plurality of eyelet fasteners and/or zippers.

Due to nature of the fabric, a compression bodysuit is very difficult to put on and is extremely tight against the body for the purpose of squeezing and compressing the user's body in order to shape the body or reduce inflammation and/or swelling. Compression body suits are often used after medical procedures. The compression bodysuit may be a full body garment with an opening to allow for urination and bowel movements.

The opening is very often not of sufficient size or configuration for urination by women without getting urine on the compression bodysuit. The opening is often not sufficient size or configuration to allow for bowel movement without getting feces on the compression bodysuit.

There are a number of devices women use to help them urinate without getting urine on the compression bodysuit. Such are usually made of a soft yet sturdy silicone material and are shaped similar to a funnel. Women use such devices while wearing a compression bodysuit in order to not get urine on the compression bodysuit. The devices physically direct urine though the devices. The current female urine devices are not designed to be used for bowel movements, and are currently not used for bowel movements because of the design of such devices does not facilitate use for bowel movements.

Adult diapers have also been worn to allow users of compression bodysuits to have a bowel movement without taking off the compression bodysuit. This is uncomfortable and not ideal as it requires the user to eventually take off the compression bodysuit to change the diaper.

The known device designs do not disclose the combined structure and function of the apparatus of the present invention. Accordingly, it would be an improvement in the art to provide an apparatus which unlike the known devices helps men and women who wear a compression bodysuit perform bowel movements without taking off the compression bodysuit without soiling the compression body suit.

SUMMARY OF THE INVENTION

The present invention relates to apparatuses for facilitating bowel movements of person wearing a compression body suit without requiring removal of the compression bodysuit and for shielding the compression body suit from bowel movements.

In particular, the apparatus of the present invention is directed to manually-placed, hygiene apparatus which draws back and holds back fabric of the compression bodysuit in the crotch or anal area of the bodysuit. The apparatus is held against the body of the user and extends a sufficient distance away from the bodysuit. The apparatus provides a sufficiently sized opening through the compression bodysuit to readily allow bowel movements to pass to the toilet or other receptacle without contacting the bodysuit.

One embodiment of the present invention comprises a plastic device which when placed retracts the compression bodysuit at the crotch or anal area of the bodysuit to protect the compression bodysuit from feces while making a bowel movement. This allows someone who wears a compression bodysuit after surgery, medical procedure or postpartum to have a bowel movement while continuing to wear their compression bodysuit. This provides the advantage of continuous uninterrupted healing or shaping of the compression bodysuit after a medical procedure by avoiding removal of the compression bodysuit to have a bowel movement thereby avoiding the lengthening of recovery time, causing inflammation, increased swelling, and/or increased pain.

While known compression bodysuits do have an opening for bowel movement, and because compression bodysuits are a support device for all body parts, the known and currently available openings in compression bodysuits are often not large enough to allow bowel movements without getting feces on the bodysuit garment. If feces gets on a compression bodysuit it has to be taken off to hand-wash and hang-dry therefore increasing the duration of time the user is without the constriction of the compression bodysuit, which could increase swelling and inflammation. Unlike the known compression suits and known accessory devices, the apparatus of the present invention provides superior, hygienic passages of feces through the opening of the compression bodysuit.

These and other features and advantages of the present invention will be set forth or will become more fully apparent in the description that follows and in the appended claims. The features and advantages may be realized and obtained by the structures outlined and particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

The apparatus of the present invention relates to devices for facilitating bowel movements of a person wearing a compression body suit without requiring removal of the compression bodysuit and for shielding the compression body suit from bowel movements.

Figure 1:
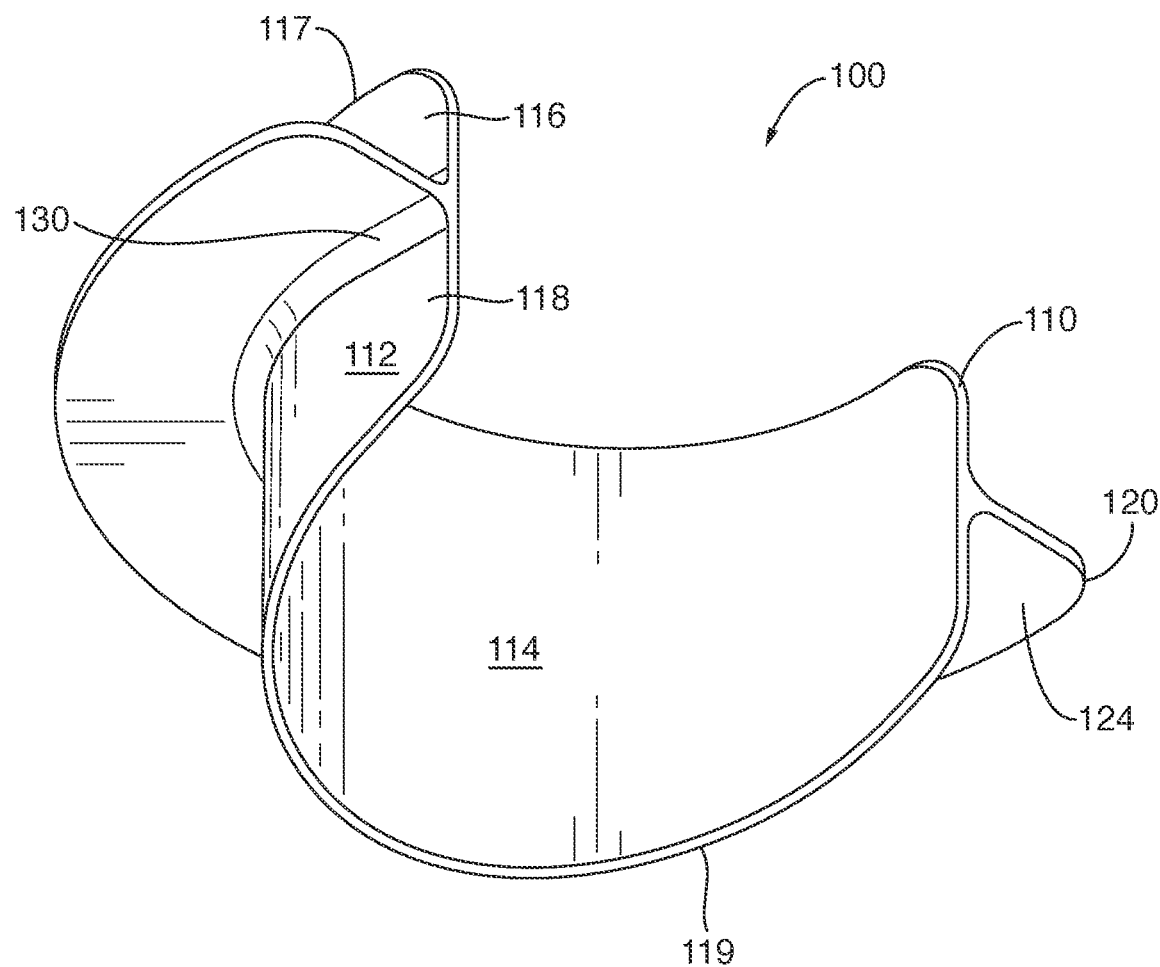
FIG. 1 illustrates a front prospective view of one embodiment of the garment retractor of the present invention.
Figure 2:
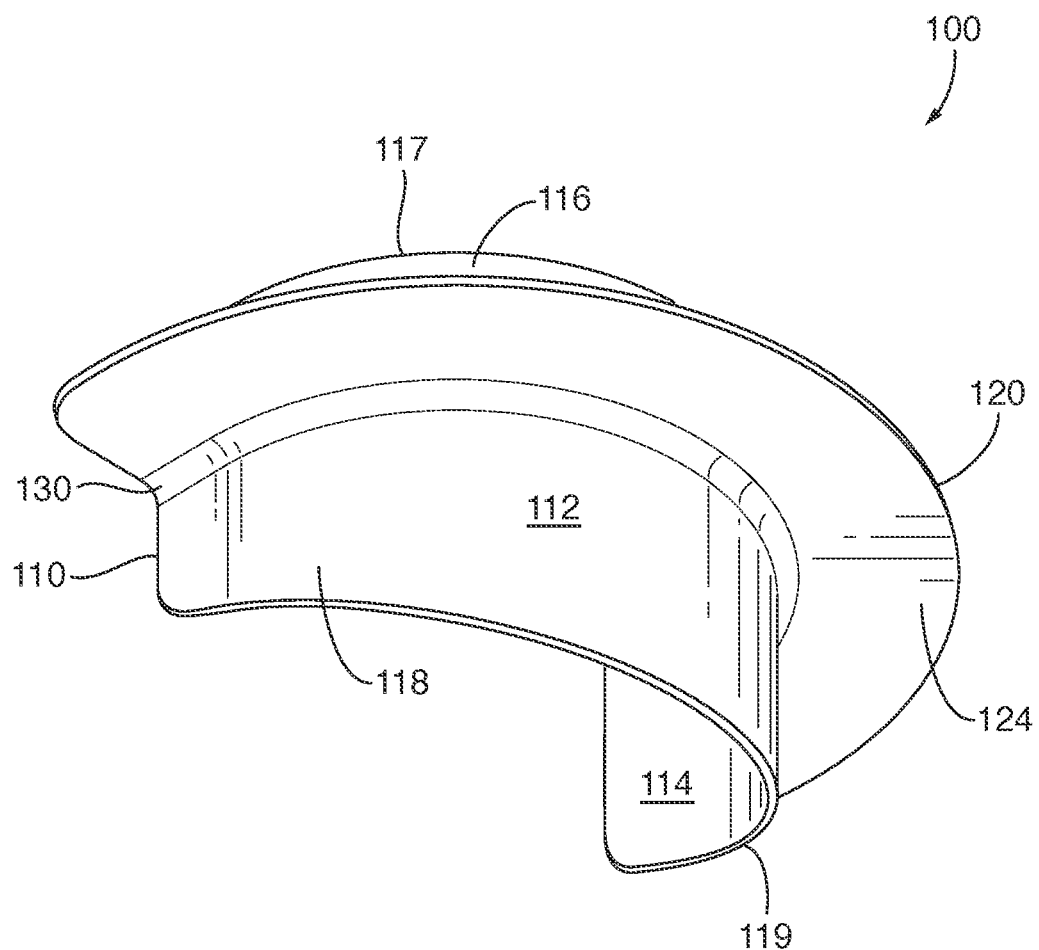
FIG. 2 illustrates a back prospective view of one embodiment of the garment retractor of the present invention.
Figure 3:
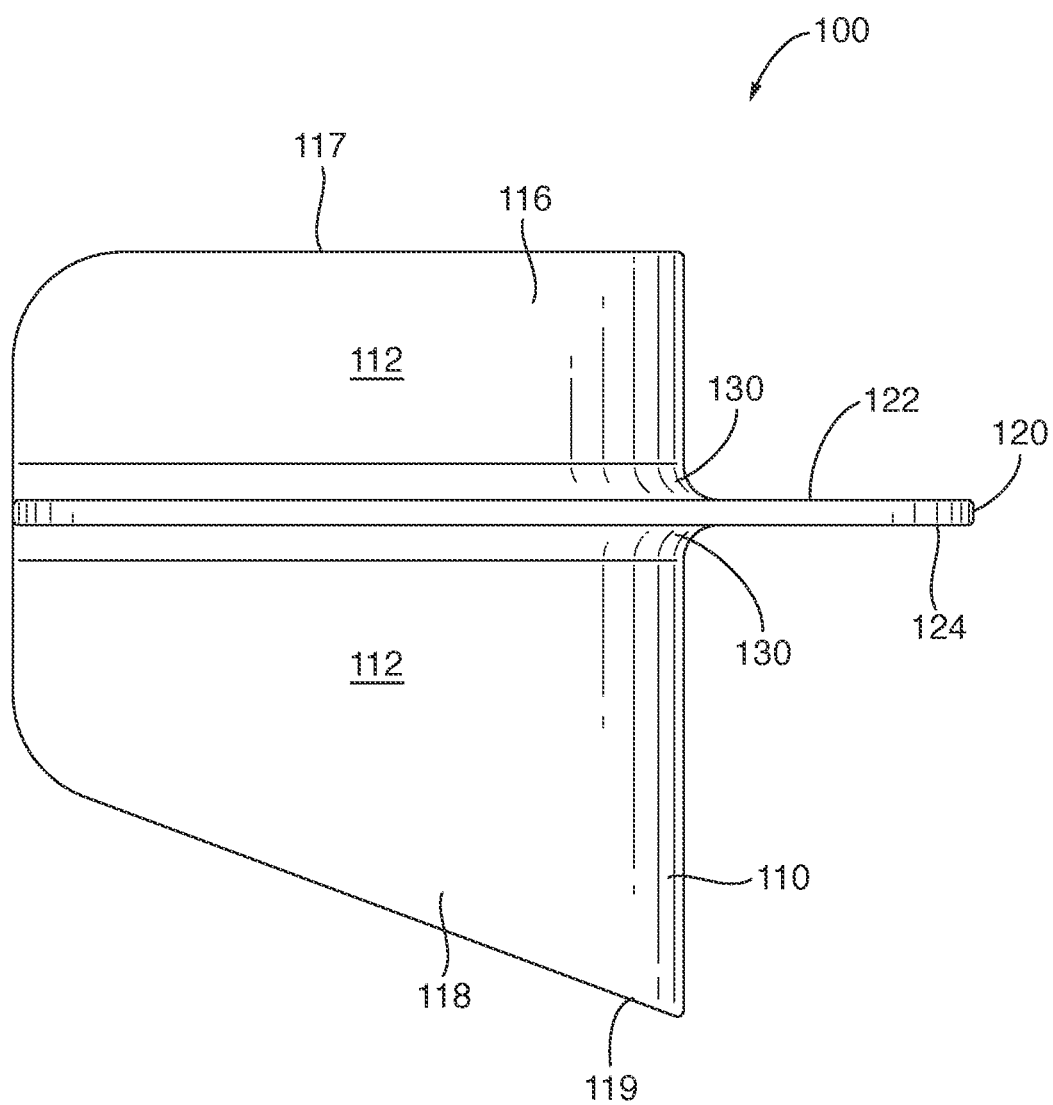
FIG. 3 illustrates a side view of one embodiment of the garment retractor of the present invention.
Figure 4:
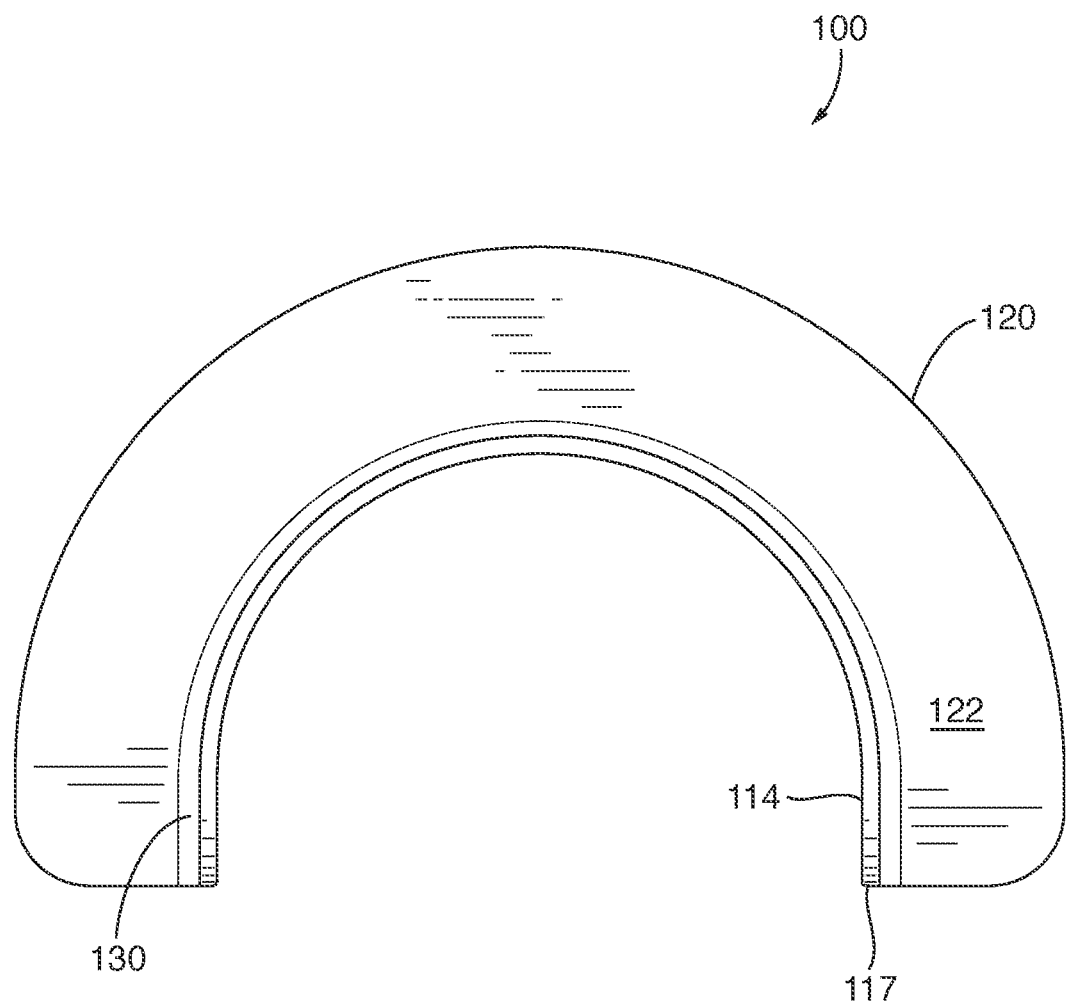
FIG. 4 illustrates a top view of one embodiment of the garment retractor of the present invention.
Figure 5:
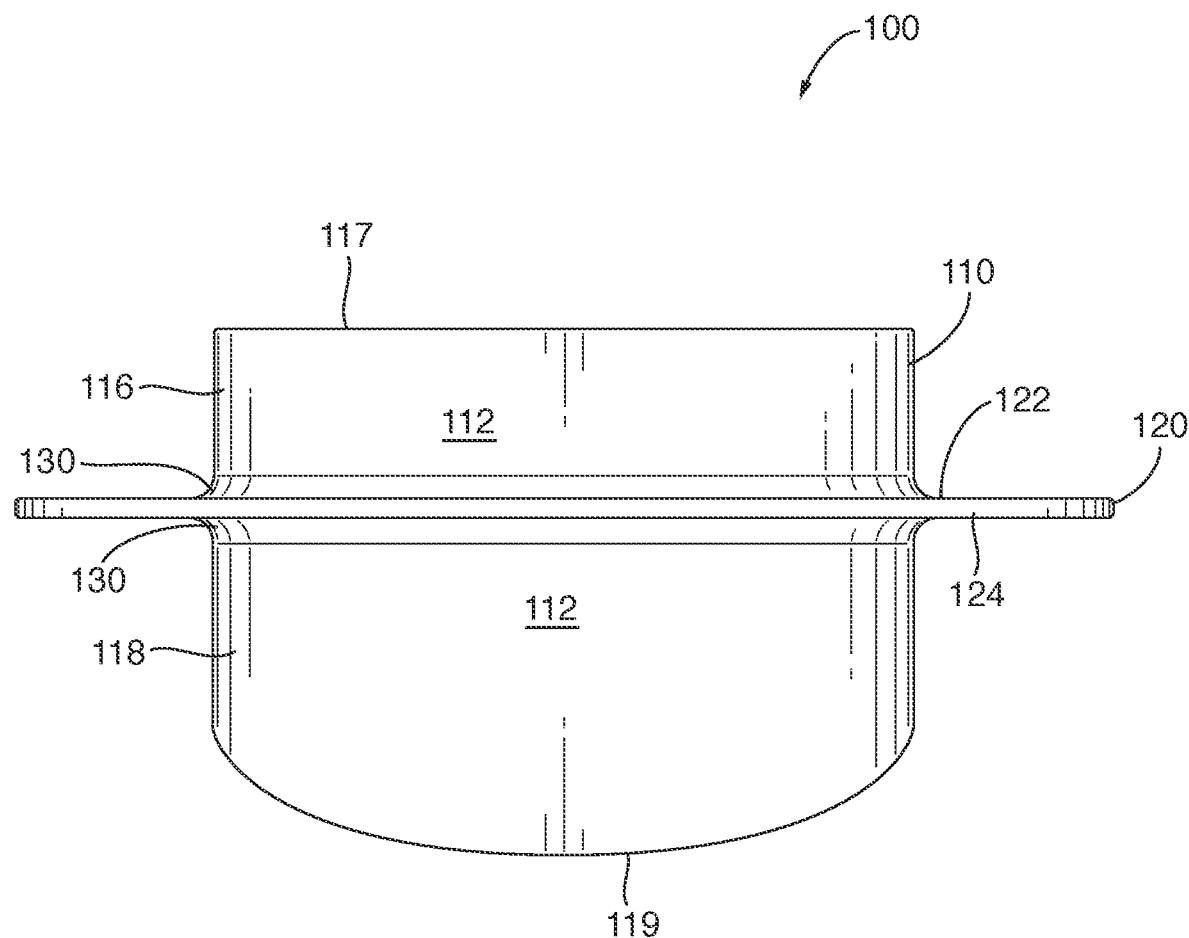
FIG. 5 illustrates a back view of one embodiment of the garment retractor of the present invention.
Figure 6:
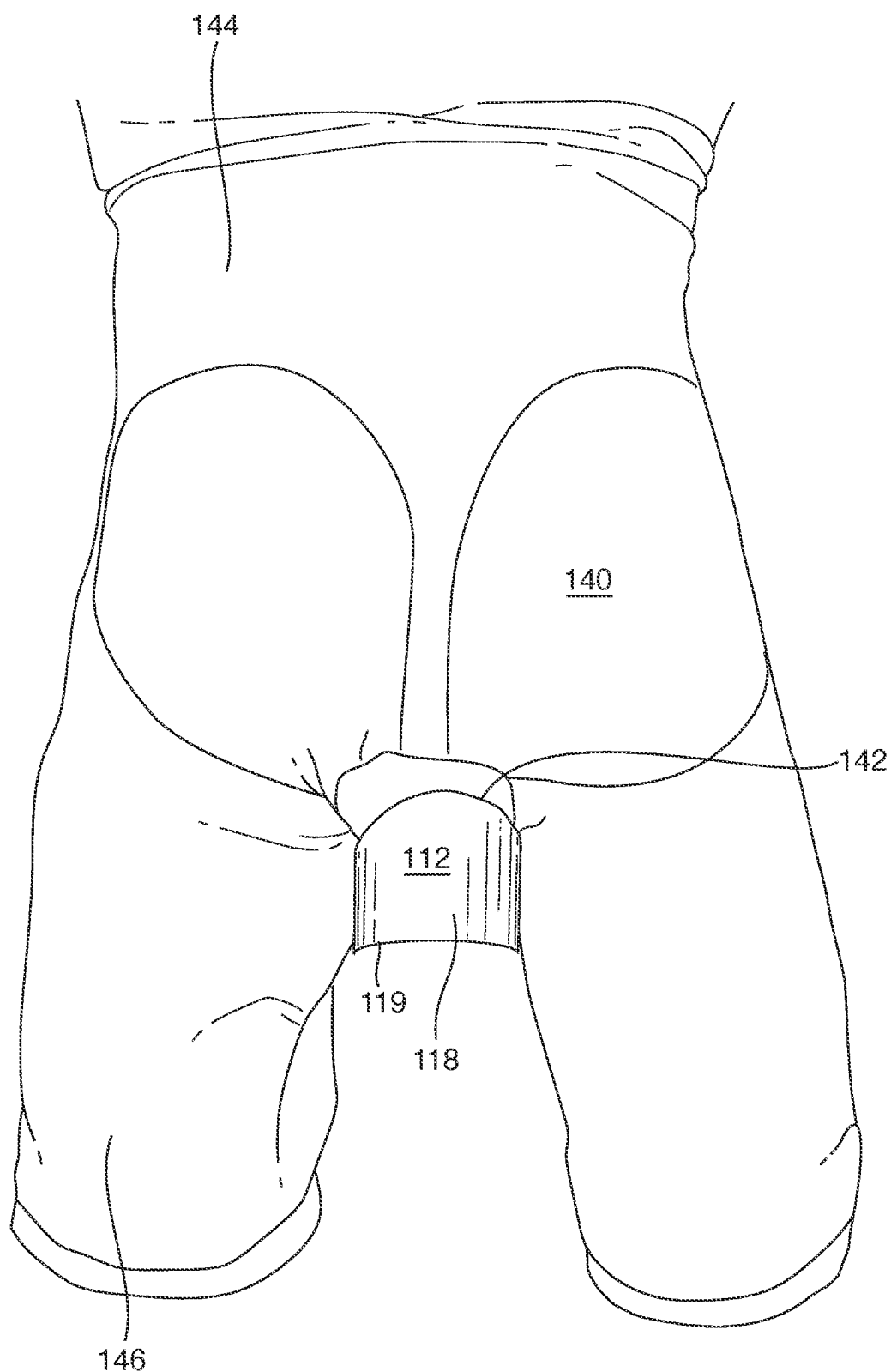
FIG. 6 depicts one illustrative placement of the garment retractor in use.

As shown in FIGS. 1-5, the apparatus of the present invention comprises a compression bodysuit retractor 100 to draw or pull back and hold back a portion of the compression bodysuit 140, see FIG. 6. Retractor 100 comprises chute or conduit wall member 110 which defines an opening, chute or shield through which feces may pass from the wearer of the compression bodysuit to the toilet or catch receptacle.

Wall member or elongate wall member 110 comprises an outer surface 112 and an inner surface 114.

Wall member or elongate wall member 110 further comprises a first wall member portion 116 and a second wall member portion 118. In use, wall member portion 116 is proximal to the wearer of the compression body suit defining proximal end 116 of wall member 110 and wall member portion 118 is distal to the wearer of the compression body suit defining a distal end 118 of wall member 110. Wall portion 116 or proximal end 116 terminates in a contact lip or seat surface 117 configured to contact the body of the user. Wall portion 118 or distal end 118 terminates in an exit edge or lip 119 away from the body of the user. Wall portion 118 or end 118 has a length sufficient to extend exit lip 119 beyond the compression body suit, see FIG. 6.

Retractor 100 may also comprise a support or retention ring 120 configured substantially normal of wall member 110. Ring 120 extends a length or distance away from wall member 110. Retention ring 120 comprises a surface 122 and a surface 124. The length of ring 120 serves as a retention wall for opening 142 of bodysuit 140 as discussed below.

Ring 120 may be configured unitary to wall member 110. Ring 120 may be configured as joined to wall member 110. In either configuration, wall member 110 and ring 120 have a transition 130 between wall member 110 and ring 120. If ring 120 is joined to wall member 110, transition 130 may comprise a weld, joint, glue, seal or any other fixing mechanism to join ring 120 to wall member 110.

In one embodiment, retractor 100 may comprise a double arch design. One arched structure is provided by wall member 110. Another arched structure is provided by ring 120. This double-arch design provides rigidity and strength sufficient to hold back the high tension of a compression bodysuit. This two-arch configuration provides a handle and hook from ring 120, and a guard and pathway from wall member 110. The substantially flat lip or seat 117 is configured to rest against the skin of the user. The opposing exit edge 119 may be angled.

While FIGS. 1-5 depict wall member 110 and ring 120 as arch shaped, it is contemplated that wall member 110 may comprise a cylindrical configuration and/or ring 120 may comprise a circular configuration. Further, while seat surface 117 is illustrated as substantially flat or planar, seat surface 117 may be configured to conform to the shape of human anatomy in any corresponding non-planar configuration. As described above, wall member 110 and ring 120 define a retention walls to maintain the desired position of the garment in use.

In one embodiment, retractor 100 may be constructed of one solid piece of molded plastic. In an alternative embodiment, retractor 100 may be constructed of a softer material such as silicone and with wall member 110 and ring 120. Retractor 100 may be constructed by joining ring 120 to wall member 110. If constructed a durable, rigid plastic, retractor 100 may be reusable. In the alternative, retractor 100 may be constructed of sufficiently rigid material to permit one-time, disposable use, such as plastic or paper.

In use, and as illustrated in FIG. 6, the user when needing to perform a bowel movement keeps the compression bodysuit 140 on and fastened. Bodysuit 140 may define an opening 142. Bodysuit 140 may also comprise a torso portion 144 and a lower limb portion 146.

When using the apparatus of the present invention, compression bodysuit 140 does not have to be loosened from the wearer. While standing, retractor 100 may be handled by wall member 110 or ring 120 using, for example, the index finger, middlefinger, and thumb of a hand. With the other hand the user can either reach around the back or the front to pull back bodysuit 140 at opening 142 in the anal or crotch area of bodysuit 140. The user may use fingers such as the index finger, the middle finger, and the thumb to pull the side of opening 142 of bodysuit 140 away from the skin. The user places retractor 100 in place by sliding at least a portion of ring 120 into the compression bodysuit with seat 117 toward the user's skin such that a portion of ring 120 is disposed between the user and bodysuit 140. The user may then use a finger of the hand that is holding the compression bodysuit to stretch and wrap compression bodysuit 140 around the uninserted portion of support ring 120 such that the repose position of opening 142 of bodysuit 140 contacts retractor 100 about wall portion 118 adjacent surface 124 of ring 120. The user releases hold of both the compression bodysuit 140 and retractor 100. Retractor 100 is held in place, see FIG. 6.

The user then sits on the toilet or above another receptacle. The user then performs a bowel movement as normally would be performed.

Once the user has completed the bowel movement and cleans himself or herself, the user may stand up and the user reaches a hand around the back or to the front to grasp outer wall 112 of wall portion 118 of retractor 110. The user may slide or urge retractor 110 forward while pulling the bodysuit 140 away from retractor 100 with the other hand to remove retractor 100.

In this way, retractor 100 makes bowel movements in compression bodysuits more comfortable, and makes the compression bodysuit more user friendly while having a bowel movement, while maintaining the cleanliness and hygiene of bodysuit 140. In one embodiment, inner wall 114 of retractor 100 is not intended to direct the passage of feces or come in contact with the feces, but wall member 110 of retractor 100 is configured to define a sufficiently large opening to allow passage of the feces into the toilet without contacting retractor 100. In an occurrence of abnormal bowel movement, retractor 100 protects or shields compression bodysuit 140 from feces.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A garment retractor for a garment worn by a person comprising:
    a wall member comprising a length, the wall member comprising a first wall member portion along the length of the wall member and a second wall member portion along the length of the wall member, the length of the wall member defining a chute or conduit to retract an anal portion of the garment, the proximal end of the first wall member defining a proximal opening of the chute or conduit, the distal end of the second wall member defining a distal opening of the chute or conduit, the distal opening being substantially the same size as the proximal opening, the first wall member defining a seat surface to receive the anal portion of the person; and
    a ring member, the ring member disposed along the length of the wall member, ring member extending away from the wall member substantially normal to the wall member, the first wall member extending proximally a first length away from the ring member terminating in the seat surface of the first wall member, and the second wall member extending distally a second length away from the ring member to an exit lip of the second wall member; and
    wherein a portion of the second length is substantially greater than the first length and is of sufficient length to extend beyond the anal portion of the garment to retract and maintain the anal portion of the garment away from the distal opening of the chute.

2. The apparatus of claim 1 wherein the wall member is configured in a non-closed arch shape.

3. The apparatus of claim 1 wherein the wall member is configured in a cylindrical shape.

4. The apparatus of claim 1 wherein the ring member is configured in a non-closed arch shape.

5. The apparatus of claim 1 wherein the ring member is configured in a circular shape.

6. The apparatus of claim 1 wherein the seat surface is substantially flat.

7. The apparatus of claim 1 wherein the seat surface conforms to the anal shape of human anatomy.

8. The apparatus of claim 1 wherein the wall member defines a retention wall to maintain a desired position of the garment in use.

9. The apparatus of claim 1 wherein the ring member extends a length or distance away from the wall member, the length of the ring defining a retention wall to maintain a desired position of the retractor when inserted between the anal portion of the person and the inside of the garment.

10. A garment retractor for a garment worn by a person comprising:
    an elongate wall member comprising a proximal end and a distal end, the elongate wall member defining a chute or conduit, the proximal end of the wall member defining a proximal opening of the chute or conduit, the distal end of the wall member defining a distal opening of the chute or conduit, the distal opening being substantially the same size as the proximal opening, the proximal end of the elongate wall member defining a seat surface to receive the anal portion of the person; and
    a retention ring, the retention ring disposed along the elongate wall member, the retention ring extending away from the elongate wall member substantially normal to the elongate wall member;
    the wall member comprising a first wall member extending proximally a first length away from the retention ring terminating in the seat surface of the wall member, and a second wall member extending distally a second length away from the retention ring to an exit lip of the second wall member; and
    wherein a portion of the second length is substantially greater than the first length and is of sufficient length to extend beyond the anal portion of the garment to retract and maintain the anal portion of the garment away from the distal opening of the chute.

11. The apparatus of claim 10 wherein the elongate wall member is configured in a non-closed arch shape.

12. The apparatus of claim 10 wherein the elongate wall member is configured in a cylindrical shape.

13. The apparatus of claim 10 wherein the retention ring is configured in a non-closed arch shape.

14. The apparatus of claim 10 wherein the retention ring is configured in a circular shape.

15. The apparatus of claim 10 wherein the seat surface is substantially planar.

16. The apparatus of claim 10 wherein the seat surface is non-planar.

17. The apparatus of claim 10 wherein the elongate wall member defines a retention wall to maintain a desired position of the garment in use.

18. The apparatus of claim 10 wherein the retention ring extends a length or distance away from the elongate wall member, the length of the retention ring defining a retention wall to maintain a desired position of the retractor when inserted between the anal portion of the person and the inside of the garment.

* * * * *